United States Patent [19]
Goddard et al.

[11] Patent Number: 5,860,970
[45] Date of Patent: Jan. 19, 1999

[54] CRYOSURGICAL INSTRUMENT

[75] Inventors: Robert William Goddard; Leslie John Penny, both of Andover, United Kingdom

[73] Assignee: Spembly Medical Limited, United Kingdom

[21] Appl. No.: 737,425
[22] PCT Filed: Mar. 31, 1995
[86] PCT No.: PCT/GB95/00740
§ 371 Date: Jul. 7, 1997
§ 102(e) Date: Jul. 7, 1997
[87] PCT Pub. No.: WO95/30380
PCT Pub. Date: Nov. 16, 1995

[30] Foreign Application Priority Data

May 10, 1994 [GB] United Kingdom .................. 9409232

[51] Int. Cl.⁶ ................................................ A61B 17/36
[52] U.S. Cl. ............................................................ 606/23
[58] Field of Search ...................................... 606/20–26

[56] References Cited

U.S. PATENT DOCUMENTS

| | | | |
|---|---|---|---|
| 3,398,738 | 8/1968 | Lamb et al. | 606/23 |
| 3,421,508 | 1/1969 | Nestrock | 606/23 |
| 3,439,680 | 4/1969 | Thomas, Jr. | 606/24 |
| 3,786,814 | 1/1974 | Armao . | |
| 3,827,436 | 8/1974 | Stumpf et al. . | |
| 4,202,336 | 5/1980 | Gerven | 606/24 |
| 4,802,475 | 2/1989 | Weshahy . | |
| 5,108,390 | 4/1992 | Potockey et al. | 606/21 |

FOREIGN PATENT DOCUMENTS

| | | | |
|---|---|---|---|
| 2101043 | 7/1972 | Germany | 606/23 |
| 449716 | 11/1974 | U.S.S.R. | 606/23 |
| 2183162 | 6/1987 | United Kingdom | 606/23 |
| 9308753 | 5/1993 | WIPO . | |

*Primary Examiner*—Lee Cohen
*Attorney, Agent, or Firm*—Renner, Otto, Boisselle & Sklar, P.L.L.

[57] ABSTRACT

A cryosurgical instrument comprises a metal cooling tip operable to be cooled by a flow of cryogenic fluid within the tip, at least a boiling region of the tip being coated with a heat-insulating coating. The presence of the heat-insulating coating can promote nucleate boiling of the fluid rather than film boiling. Nucleate boiling within the tip provides a greater cooling efficiency of the tip than film boiling.

24 Claims, 5 Drawing Sheets

CRYOSURGICAL INSTRUMENT

FIELD OF THE INVENTION

This invention relates to cryosurgical instruments.

BACKGROUND

It is known to use cryosurgical instruments in surgical operations in which living tissue is destroyed (or ablated) by cooling the tissue to well below the freezing point of water (e.g. −20° to −30° Centigrade).

WO 93/04647 discloses a cryosurgical instrument in which a metal tip of a cryosurgical probe is cooled by supplying liquid nitrogen to the interior of the tip.

In such an instrument, when the liquid nitrogen reaches the interior of the metal tip, it starts to boil. There are two possible modes of boiling which can take place. If so-called 'film' boiling occurs, a film of nitrogen gas forms between the inner surface of the metal tip and the boiling liquid nitrogen. This film of gas reduces the heat conduction between the boiling liquid and the body of the tip and thus reduces the cooling efficiency of the instrument. The other possible mode of boiling is referred to as 'nucleate' boiling. In this mode the film of gas does not form, so the heat conduction between the boiling liquid and the body of the tip is much better, and the cooling efficiency of the tip is thus improved.

Although nucleate boiling provides a more efficient cooling operation, it is often difficult to control the mode of boiling reliably so that nucleate boiling takes place. In particular, film boiling often occurs for some time at the start of a period of operation of a cryosurgical instrument. Because the cooling efficiency is lower when film boiling takes place, surgical procedures in which tissue has to be cooled can take longer. This can be both hazardous (by increasing the time during which a patient must be anaesthetized), expensive and inconvenient.

SUMMARY OF THE INVENTION

This invention provides a cryosurgical instrument comprising a metal cooling tip operable to be cooled by the boiling of a cryogenic fluid, predominantly within a boiling region of the tip, in which the exterior of at least the boiling region is coated with a heat-insulating coating.

The invention addresses the problem of achieving more reliable nucleate boiling in a cryosurgical instrument by the counter-intuitive step of adding a heat-insulating coating to the exterior of the cooling tip. It has been found that such a coating can actually promote nucleate boiling (rather than film boiling) within the cooling tip.

The invention involves coating substantially the entire boiling region of the tip. In fact, for ease of application of the coating, in preferred embodiments the entire exterior surface of the tip can be coated. This contrasts with precious tips (e.g. those disclosed in U.S. Pat. No. 3,827,436) in which cooling regions of the tip are masked to prevent unwanted freezing of tissue by those particular regions. In the invention, however, the coating extends over active (cooling) regions of the tip which are still used for tissue ablation.

Preferably the instrument comprises means for supplying the cryogenic fluid to the interior of the tip.

Although the use of other cryogenic fluids could be envisaged (such as freon 14, freon 22, freon 13, liquefied air and normally gaseous hydrocarbons), it is preferred that the cryogenic fluid is liquid nitrogen. Liquid nitrogen is reasonably cheap, readily available, inert and relatively innocuous when vented to the atmosphere.

Various heat insulating coatings could be used, such as thin plastics coatings. However, it is preferred that the coating is a polytetrafluoroethane coating.

Preferably the coating is less than about $30 \times 10^{-6}$ meters thick.

Preferably the tip is made of silver. Silver is a good heat conductor and can also tend to discourage the growth of potentially harmful bacteria on the tip.

It is preferred that the instrument comprises a probe handle and a silver probe shaft linking the probe handle and the tip. The silver shaft has the advantages described above and can also act to conduct body heat to the tip when it is necessary to thaw the tip.

To assist in thawing the tip when required, so that the instrument can be removed from a patient's tissue, it is preferred that the instrument comprises means for supplying gas at greater than 0° Centigrade to the interior of the tip.

In order to avoid unwanted cooling of the shaft, it is preferred that the probe shaft comprises a cryogenic fluid supply conduit surrounded by an evacuated heat-insulating chamber.

Preferably the tip comprises a tip casing and a metal conduit within the tip casing and thermally connected to the tip casing to allow the flow of cryogenic fluid along the metal conduit and between the metal conduit and the tip casing. This structure, in which the conduit acts as a heatsink, has been found advantageously to promote nucleate boiling rather than film boiling.

Viewed from a second aspect this invention provides a cryosurgical instrument comprising a metal cooling tip operable to be cooled by a flow of a cryogenic fluid within the tip, in which the tip comprises a tip casing and a metal conduit within the tip casing and thermally connected to the tip casing to allow the flow of cryogenic fluid along the metal conduit and between the metal conduit and the tip casing.

BRIEF DESCRIPTION OF THE DRAWINGS

The invention will now be described by way of example with reference to the accompanying drawings, throughout which like parts are referred to by like references, and in which.

DETAILED DESCRIPTION

Figure 1:
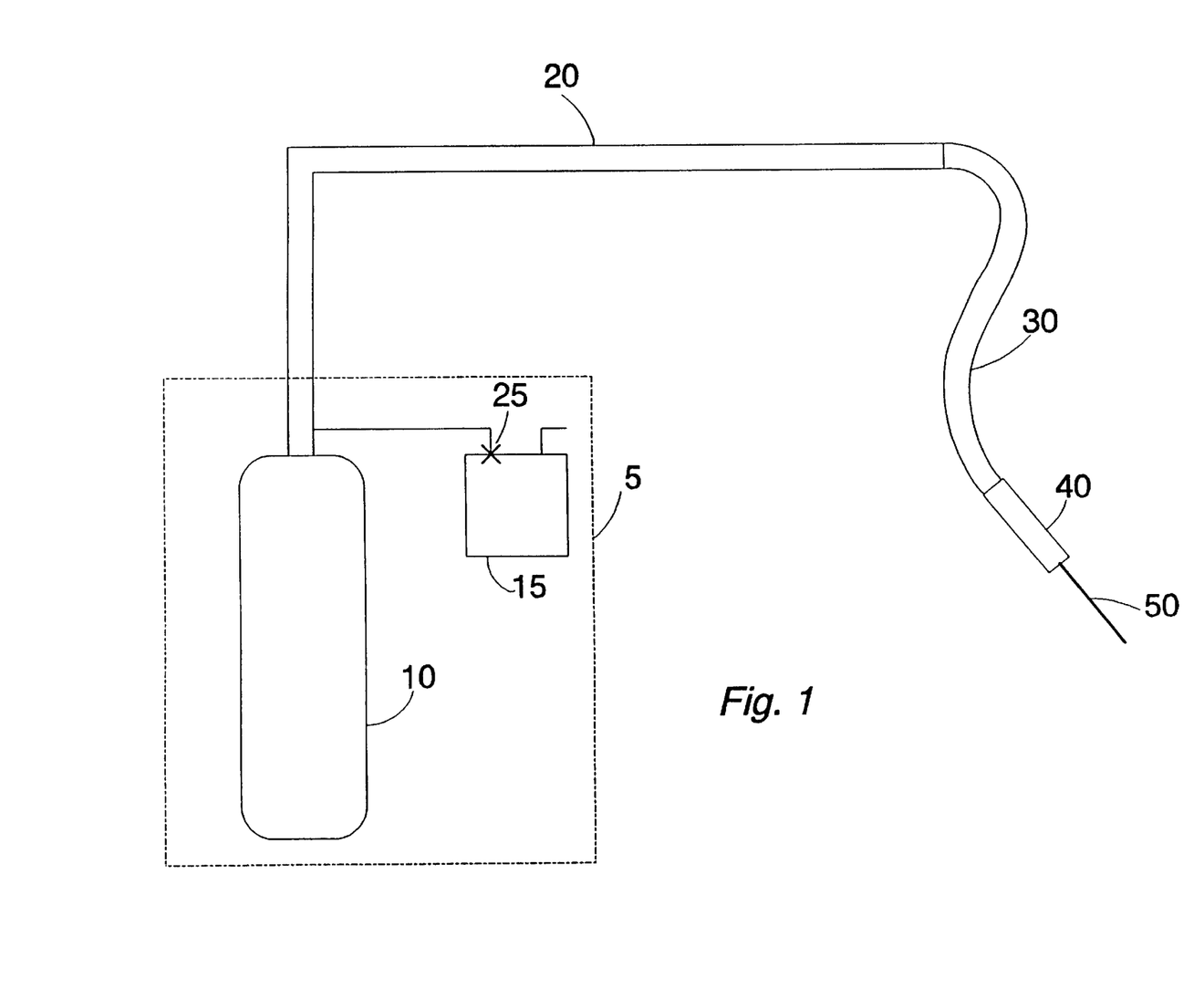
FIG. 1 is a schematic diagram of a cryosurgical probe system.

FIG. 1 is a schematic diagram of a cryosurgical probe system. The cryosurgical probe system is suitable for use in surgical operations in which living tissue is destroyed (or ablated) by cooling the tissue to well below the freezing point of water (e.g. −20° to −30° Centigrade).

A cryogenic fluid, such as liquid nitrogen, is stored in a dewar vessel 10 forming part of a fluid supply apparatus 5. Alternative cryogenic fluids include freon 14, freon 22, freon 13, liquefied air and normally gaseous hydrocarbons (although inert fluids are preferred to flammable fluids).

The cryogenic fluid is supplied via an overhead connecting tube 20 and a flexible connecting tube 30 to a probe handle 40 and eventually to a probe tip 50. The flexible connecting tube 30 is linked to the overhead connecting tube 20 by a releasable connector (see FIGS. 4a, 4b, 4c, 5a and 5b). This allows the probe and flexible connecting tube to be steam sterilised for re-use.

The cryogenic supply apparatus 5 also has a by-pass exhaust chamber 15. This is a liquid trapping chamber vented to the atmosphere. Its role is to prevent the potentially hazardous direct venting of liquid nitrogen from a by-pass return path (described below) to the atmosphere. Entry into the chamber 15 is controlled by a by-pass salve 25 mounted on the chamber 15.

When the probe system is in use during a surgical operation in an operating theatre, the fluid supply apparatus 5 is placed a short distance away from an operating table or other support for the patient. The overhead connecting tube 20 allows the transfer of cryogenic fluid between the fluid supply apparatus 5 and the cryosurgical probe held by the surgeon, without obstructing the surgeon's access to the patient. The overhead connecting tube 20 may be a rigid structure in its own right, or may be a flexible or semi-flexible tube supported on a suitable supporting frame (not shown).

In use, the probe tip is inserted into bodily tissue to be destroyed (for example, a part of the patient's liver) and cryogenic fluid is supplied from the dewar vessel 10 to the interior of the probe tip 50. This causes the probe tip 50 to be cooled, which in turn cools the bodily tissue into which the probe tip 50 is inserted. Over a period of a few minutes, a volume of the bodily tissue surrounding the probe tip 50 is cooled to about −20° to −30° Centigrade, killing the cells in that volume of tissue. When the required volume of tissue has been cooled in this way, the probe tip 50 can be allowed to thaw, either through conduction of bodily heat from the patient or by passing a heated gas into the probe tip 50. The heated gas can be generated by passing gas from a gas storage cylinder (not shown) through an electric heating element (not shown). The probe tip is then withdrawn from the bodily tissue. If necessary, the procedure outlined above may be repeated a number of times at different locations in the body or in a particular organ if a particularly large volume of tissue is to be destroyed.

The cryogenic fluid remains inside the probe tip 50 during the cooling process. In other words there is no potentially dangerous contact between the cryogenic fluid and the patient's bodily tissue.

Figure 2:
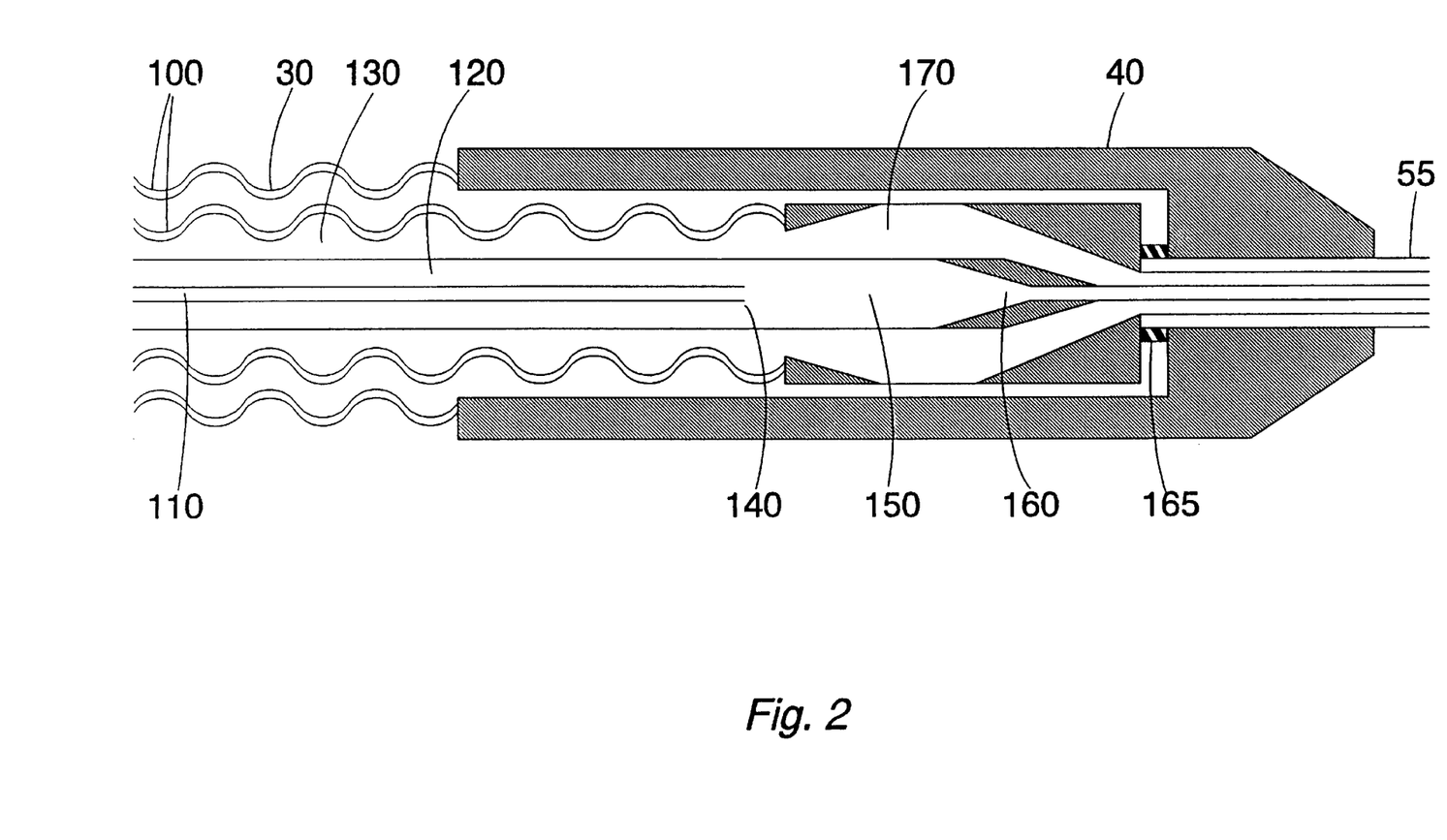
FIG. 2 is a schematic diagram of a cryosurgical probe handle.
Figure 3A:
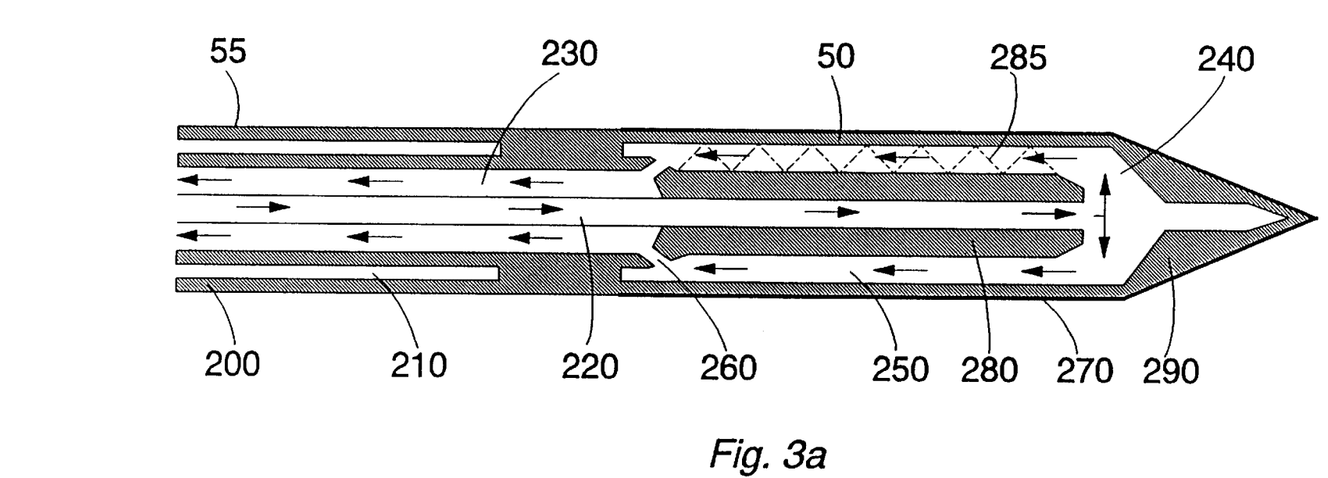
FIGS. 3a and 3b are enlarged schematic diagrams of a cryosurgical probe tip.
Figure 3B:
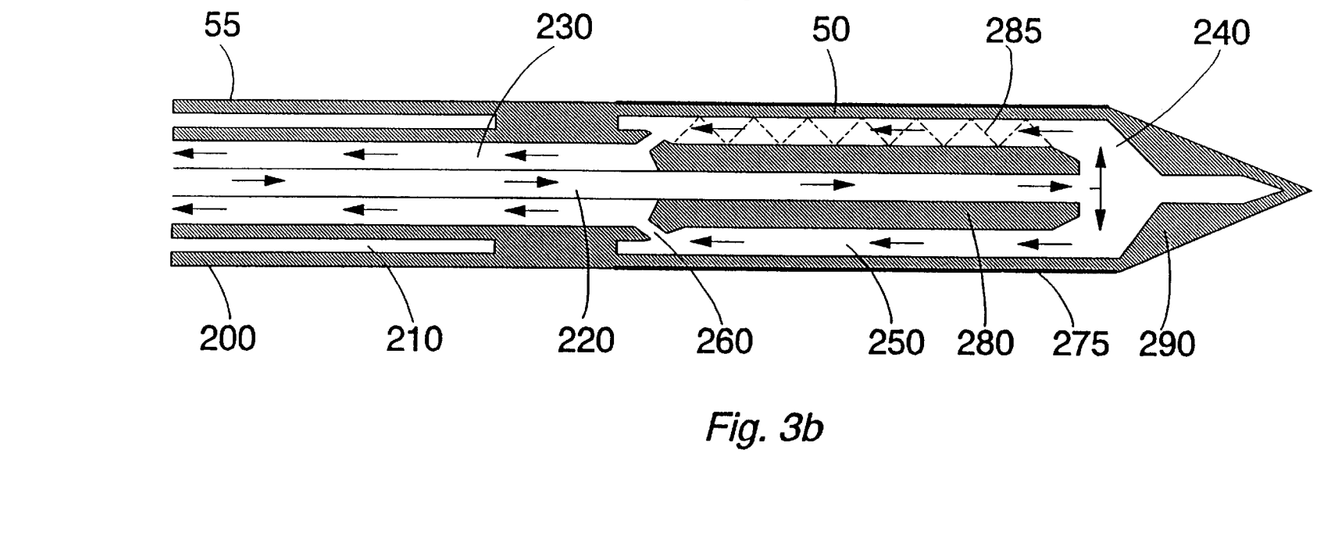

FIG. 2 is a schematic diagram of the probe handle 40, and FIGS. 3a and 3b are enlarged schematic diagrams of the cryosurgical probe tip 50.

Referring to FIGS. 2 and 3a, the probe handle 40 is connected to the flexible connecting tube 30 for the supply and exhaust of cryogenic fluid. The flexible connecting tube 30 is in fact a coaxial structure of several tubes. At the outside of the flexible connecting tube 30 are two skins 100, each formed of a double-walled structure of flexible corrugated tubing. This double-skinned structure provides good heat insulation to prevent the outside of the flexible connecting tube 30 becoming hazardously cold when the probe is in use. Inside the inner skin 100 are two coaxial PTFE (polytetrafluoroethane) tubes, namely a cryogenic fluid supply tube 110 and, surrounding the cryogenic supply tube 110, a by-pass tube 120. A region 130 between the outside of the by-pass tube 120 and the inner skin 100 forms an exhaust gas passage. Seals 165 are provided to terminate the annular space between the skins 100.

Cryogenic fluid supplied through the fluid supply tube 110 emerges at high velocity through a fluid outlet 140. The fluid emerges into a transfer chamber 150, from which some of the fluid may return towards the fluid supply apparatus along the by-pass tube 120, and some may pass through a convergent nozzle 160 in a direction towards the probe tip 50.

For the first few minutes of operation of the probe system, the by-pass tube 120 is connected via the by-pass valve 15 (to be described below) to an atmospheric air vent. This means that a significant proportion of the cryogenic liquid emerging from the fluid outlet 140 is able to return along the by-pass tube 120.

This arrangement means that the flow rate or fluid velocity of cryogenic fluid emerging from the outlet 140 can be increased by allowing some of the fluid to vent via the by-pass tube 120. The need for this arises because the fluid passing through the convergent nozzle 160 has to pass along a narrow fluid supply passage towards the tip 50. If the fluid velocity is increased by using the by-pass tube and valve, the initial flow of cryogenic fluid along the narrow fluid supply passage can be made much more reliable.

In addition, the by-pass system allows bubbles of gas formed in the fluid supply tube 110 to escape through the by-pass path, rather than passing the gas through the cooling tip 50. This diversion of the gas bubbles away from the tip can assist in cooling the tip down during the early stages of operation, since the cryogenic fluid has a much higher heat capacity per unit volume in liquid form than in gaseous form.

The separation of gas and liquid cryogenic fluid in the chamber 150 is helped by the relative positioning of the fluid outlet 140 the convergent nozzle 160 and the entrance to the by-pass tube 120. In a stream of gas and liquid cryogenic fluid, the liquid will have a much greater momentum than the gas, because it is about 600 times more dense than the gas phase. This means that the liquid is more likely to continue across the chamber 150 from the outlet 140 into the convergent nozzle 160, whereas the gas is more likely not to cross the chamber 150. The by-pass tube is connected to an atmospheric air vent and so provides a low-pressure, wide bore path for the gas to escape, whereas the convergent nozzle leads to a narrower bore, higher pressure path. Accordingly, the gas tends to follow the by-pass path.

The by-pass passages throughout the system are coaxial, surrounding the fluid supply tubes. This means that during the initial period of operation when the by-pass valve 25 is open, the fluid supple tubes are cooled by the flow of cryogenic fluid along the by-pass passages. Cooling the supply tubes is important to allow the cryogenic fluid to reach the probe tip 50 while still in liquid form (for efficient cooling of the probe tip 50), rather than as a gas.

After a predetermined time period in operation (e.g. 3 to 5 minutes) a control circuit (not shown) closes the by-pass valve 25 and so prevents further flow of cryogenic fluid along the by-pass tube 120. After this period in operation, the narrow fluid supply passage is full of the cryogenic fluid and is sufficiently cool that further fluid can flow easily down the passage. This means that the by-pass path is no longer needed, so it is shut off to avoid an unnecessary waste of the cryogenic fluid.

The by-pass valve 25 can also be controlled in response to the flow rate of exhaust fluid from the probe tip 50. If a problem arises which cuts down the flow of cryogenic fluid into the probe tip 50, this can be detected as a drop in the exhaust flow rate below a threshold rate, by means of a suitable flow rate detector (not shown). In order to increase the fluid flow to the probe tip 50, the by-pass valve 25 can then be opened, either for a predetermined time or until the exhaust flow rate reaches the threshold rate. As described above, this has the effect of increasing the fluid velocity as the fluid approaches the convergent nozzle 160, and so increasing the fluid flow rate into the probe tip 50.

During operation when the by-pass valve is closed, the consumption of cryosurgical fluid by the probe tip 50 is about 0.25 liters per minute.

Exhaust fluid emerging from the tip 50 passes into a coaxial exhaust chamber 170 which communicates with the exhaust passage 130.

FIG. 3a is an enlarged schematic diagram of the probe tip 50. The probe tip 50 is connected to the handle 40 by a probe shaft 55. The probe shaft 55 has an outer wall 200 made of silver which surrounds a coaxial vacuum chamber 210. The vacuum chamber 210 provides a degree of heat insulation between the cryogenic fluid passing inside the shaft 55 and the bodily tissue in contact with the shaft 55. This means that the freezing effect takes place primarily at the tip of the probe tip 50, rather than along the shaft 55, thus giving the surgeon better control over the location to be frozen. Within the shaft 55, there is a coaxial structure of a PTFE supply tube 220 and a surrounding exhaust passage 230. The returning exhaust fluid along the exhaust passage 230 can help to keep the incoming fluid cool.

The supply tube 220 continues as far as a heatsink 280 which then carries the cryogenic fluid to a chamber 240. The chamber 240 communicates with exhaust passages 250. Exhaust fluid passing through the exhaust passages 250 flows into the exhaust passage 230 through a series of spaced exhaust apertures 260. The path of fluid into the tip 50 and back along the exhaust passage 230 is shown schematically in FIGS. 2 and 3a using direction arrows.

When the cryogenic fluid emerges into chamber 240, it starts to boil. There are two possible modes of boiling which can take place. If so-called 'film' boiling occurs, a film of nitrogen gas forms between the inner surface of the chamber 240 and the boiling liquid nitrogen. This film of gas reduces the heat conduction between the boiling liquid and the silver body of the tip 50 and thus reduces the cooling efficiency of the probe. The other possible mode of boiling is referred to as 'nucleate' boiling. In this mode boiling takes place at discrete bubble-forming sites at the liquid-solid boundary. The film of gas does not form, so the heat conduction between the boiling liquid and the outer silver body of the tip 50 is much better, and the cooling efficiency of the tip is thus improved.

It has been found that, unexpectedly, the nucleate boiling process can be encouraged by providing a thermally insulating coating on at least a part of the outer surface of the tip 50.

In the embodiment shown in FIG. 3a, a thin PTFE coating 270 on the entire outer surface of the tip 50 is used. The coating is about 10 to $20 \times 10^{-6}$ meters thick (preferably less than about $30 \times 10^{-6}$ meters thick).

In an alternative embodiment shown schematically in FIG. 3b, a similar insulating coating 275 is applied to a "boiling" region of the tip. This region is a part of the tip in which the liquid tends to boil, namely the passages along the milled flats of the screw-threaded connection 285. In this boiling region, the cryogenic liquid is in close thermal contact with tissue surrounding the tip, which contrasts with the insulated supply and exhaust passages 220, 230, where the liquid is relatively thermally isolated from ambient conditions. It has been found that coating the circumference of the tip over substantially this boiling region encourages the nucleate boiling referred to above.

Another factor which has been found to increase the likelihood of nucleate rather than film boiling is the construction of the cooling tip 50. Before the cryogenic fluid reaches the chamber 240, it passes inside the heatsink 280. (Before reaching the heatsink 280, the fluid was passing along the heat-insulating PTFE supply tube 220). The heatsink 280 is made of silver and is thermally connected by a screw thread connection (shown schematically as 285) to the outer silver casing 290 of the cooling tip. Longitudinal flats are milled on the heat sink 280 to form the exhaust passages 250. This technique of passing the cryogenic fluid either side of a heatsink thermally connected to the outer wall of the cooling tip 50 has been found to promote nucleate rather than film boiling within the cooling tip.

The outer silver wall 200 of the probe shaft 55 has a number of beneficial effects. It is in thermal contact with both the patient's tissue and the tip 50, and so it can conduct body heat towards the tip 50 to assist in defrosting the tip 50. It can act as a heat sink to help the shaft remain unfrozen even when the tip 50 is cooled. Also, the silver material helps to prevent corrosion of the shaft 55. This is important in a re-usable device.

Figure 4A:
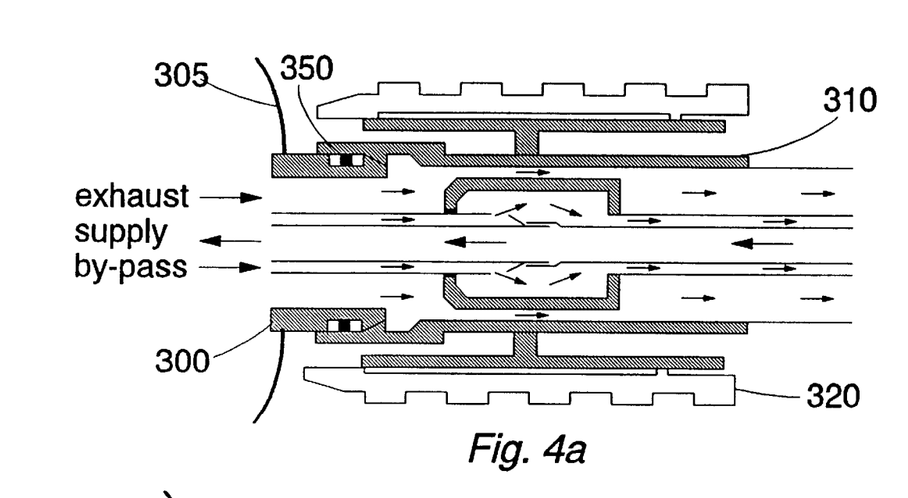
FIGS. 4a, 4b and 4c are schematic diagrams of a cryogenic fluid connector.
Figure 4B:
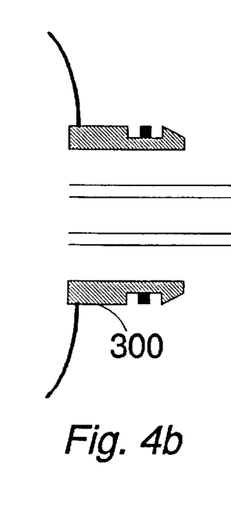
Figure 4C:
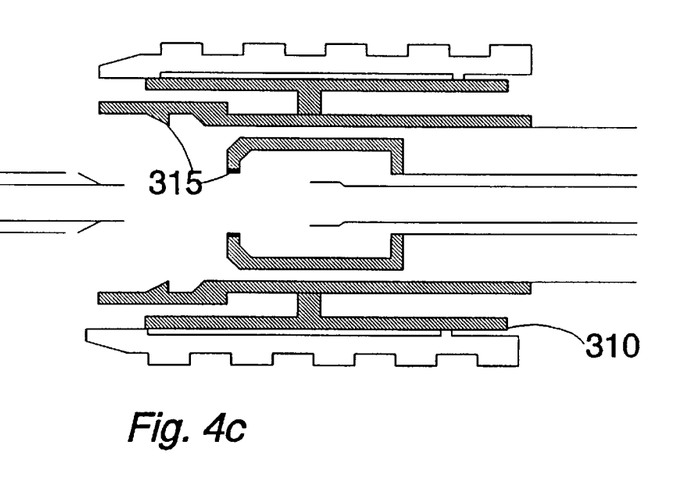

FIGS. 4a, 4b and 4c are schematic diagrams of a cryogenic fluid connector. The connector is formed of two complementary connectors, a first connector 300 linked to the flexible connecting tube 30 and a second connector 310 linked to the overhead connecting tube 20. FIG. 4a shows the first and second connectors mated together, FIG. 4b shows the first connector and FIG. 4c shows the second connector.

In FIG. 4a, the path of fluid flow in the supply, by-pass and exhaust passages is indicated by arrows.

The connectors are locked together by a bayonet fixing formed by pins (350) on the first connector engaging in angled bayonet slots (not shown on FIGS. 4a, 4b and 4c) in the second connector. The two connectors are thus linked together by pushing the first connector into the second connector, and then twisting the first connector with respect to the second connector.

Sealing rings are provided at the mating surfaces 315 of the connectors.

The connector 310 has a resiliently biased sleeve 320 which overlies the bayonet connection and prevents the connection being disconnected. The operation of the sleeve 320 is illustrated in FIGS. 5a and 5b.

Figure 5A:
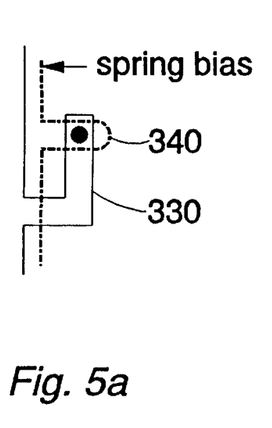
FIGS. 5a and 5b are schematic diagrams illustrating the operation of the cryogenic fluid connector of FIGS. 4a, 4b and 4c.
Figure 5B:
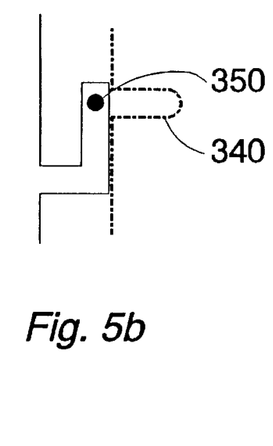

FIGS. 5a and 5b are schematic diagrams showing a bayonet slot 330 in the second connector, a retaining slot 340 formed by or connected to the sleeve 320, and a bayonet pin 350 of the first connector. (For clarity of FIGS. 4a to 4c, the retaining slot 340 has not been shown in these Figures. The retaining slot could be formed in the actual sleeve itself, or in a plate or other member attached to the sleeve).

When the pin 350 is pushed into the opening of the slot 330, it pushes against the spring-biased sleeve 320 until the pin has reached the bottom of the slot 330. The pin can then slide along the slot 330 during the rotational movement of the first and second connectors. During this movement the sleeve 320 is held back against the spring bias. However, when the pin reaches the retaining slot 340, the sleeve can return to its rest position and the pin is retained by the combination of the slot 330 and the retaining slot 340. The pin is no longer free to rotate, and so is captive between the slot 330 and the slot 340. This situation is shown in FIG. 5*a*.

Accordingly, to lock the connector as shown in FIG. 5*a*, it is necessary for an operator to touch only the first connector 300. If this connector has been sterilised then a sterile operator or 'scrub nurse' can safely lock the two connectors together without having to touch the second (non-sterile) connector 310.

A flange 305 is provided to shield the operator's hand from accidentally touching the second connector during the connection process.

In order to unlock the two connectors, the sleeve 320 must be manually pushed against the spring bias into a position shown in FIG. 5*b*. At this stage the surgical procedure is over, so it is safe for a (non-sterile) operator to touch the sleeve 320. Once the sleeve has been pushed back, the first connector can be rotated and withdrawn to free the pin 350 from the slot 330. The sleeve is made of a plastics material, to reduce the danger of the sleeve freezing to the operator s hand when touched.

The connector 310 incorporates an electric heater (not shown), which is energised at least during the time when the cryogenic fluid is passed through the connector. The heater reduces the chance of moisture in or on the connector freezing and temporarily preventing the connector from being disconnected.

Figure 6:
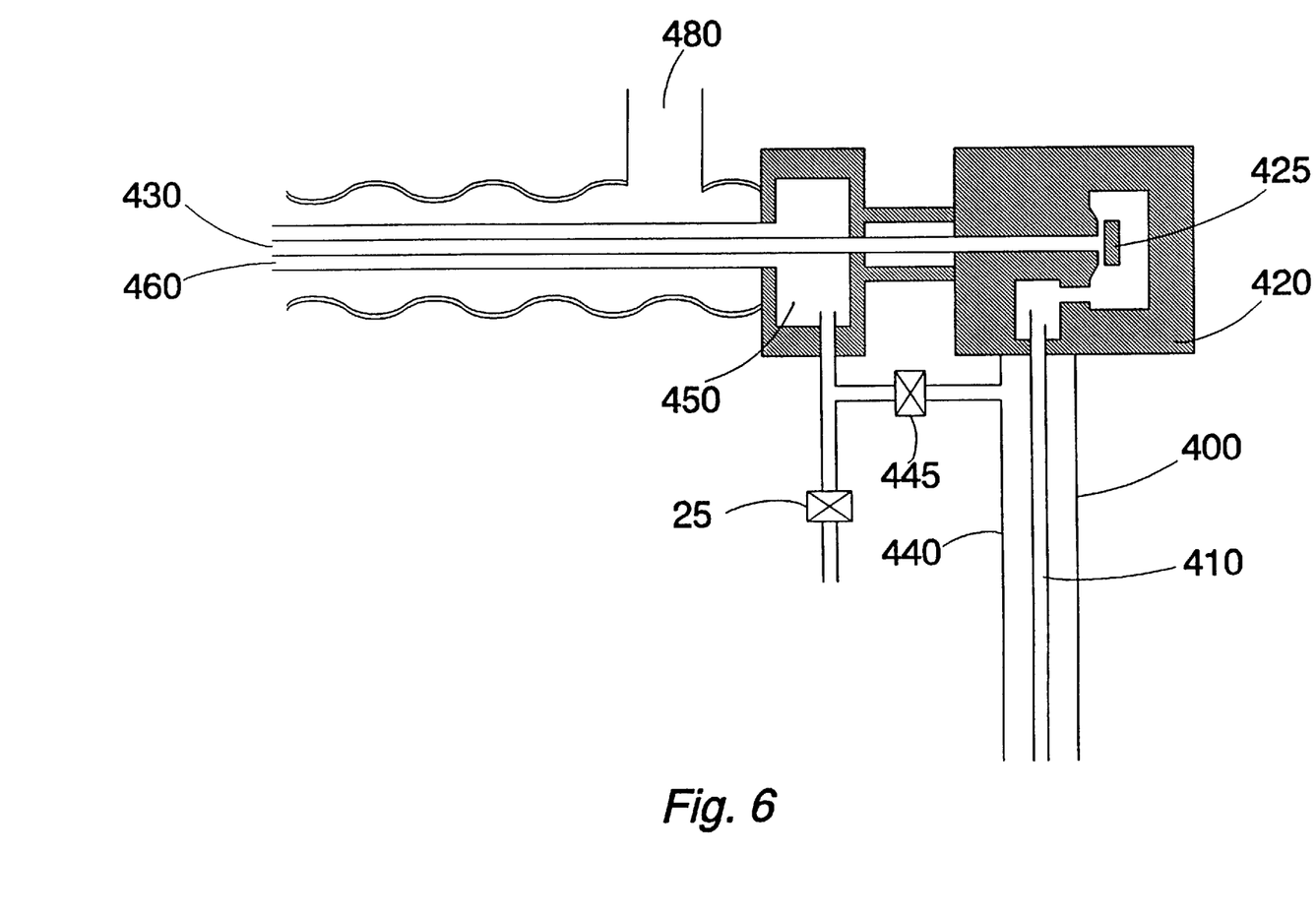
FIG. 6 is a schematic diagram of a cryogenic fluid supply apparatus.

FIG. 6 is a schematic diagram of part of the cryogenic fluid supply apparatus 5 of FIG. 1.

A dip tube 400 extends into the dewar vessel 10, to a level below the level of the cryogenic fluid in the dewar vessel. In normal operation, the cryogenic fluid to be supplied to the probe tip 50 passes along an axial supply passage 410, into the interior of a valve 420, and from the valve 420 into the axial supply passage 430 of the overhead connecting tube 20. The valve 420 can be opened and closed by means of a solenoid controlled ruby or PTFE seal 425.

A second outlet from the dewar vessel is also provided, along an outer coaxial passage 440 in the dip tube 400. During quiescent operation when the dewar vessel is pressurised but the cooling tip is not being cooled (i.e. cryogenic liquid is not being supplied to the tip), this outlet provides a purging flow of cool gas through the various connecting tubes, the probe tip 50, and the exhaust passages of the cryosurgical probe system. The purging gas is actually generated by the liquid nitrogen in the dewar vessel boiling very gently.

The passage 440 is connected, via a flow restricting valve 445, to a chamber 450 which communicates with the by-pass return path 460 from the probe handle 40.

The by-pass valve 25 selectively vents or blocks fluid output from the chamber 450, as described above. When the probe system is not in use, the by-pass valve is closed and so purging gas flows at a low flow rate into the chamber 450 and then along the by-pass passages towards the probe handle 40 (i.e. in the opposite direction to the direction in which cryosurgical fluid flows along the by-pass passages when the by-pass valve is open). When the purging gas reaches the probe handle 40, it passes along the supply tube 220 of the probe shaft 55 to the probe tip 50 and then returns along the exhaust passages towards the fluid supply apparatus. The exhaust passages communicate with an exhaust vent 480 at the fluid supply apparatus.

The purging gas serves three main purposes. First, it can help to prevent the ingress of moisture into the system (in particular, through the exhaust vent 480), by maintaining a small but steady flow of gas out of the exhaust vent 480. Second, the small flow along the dip tube 400 can help to keep the dip tube cool, thus reducing the cool down time when the system is first used. Third, in a re-usable probe some moisture can become trapped in the cooling tip during a steam sterilisation process. The purging gas can help to drive out this trapped moisture. Since the purging gas is generated by boiling off liquid nitrogen, it is very dry indeed. It has been found that such extremely dry gas can actually tend to absorb moisture in the tubes.

A further use of the purging gas is obtained by placing a pressure sensor (not shown) to measure gas pressure along the by-pass passages, at any point between the gas outlet of the flow restricting valve 445 and the connector 310 (linked to the overhead connecting tube). For example, the pressure sensor could be connected to communicate with the chamber 450.

This pressure detector has two roles. It can be used to detect whether the probe is connected at the connector 310, as a safety feature to prevent cooling operation of the system being started without a probe in place to receive the cryogenic fluid. As an additional safety feature, the pressure detector can be used to detect blockages or malfunctions in the fluid passageways, before cooling operation is initiated.

These safety features rely on detecting changes in pressure in the by-pass passages. When the system is not in use, with purging gas flowing along the by-pass passages, if the probe is not connected the gas pressure along those passages will be substantially atmospheric ($10^5$ Pa). When a correctly functioning probe is connected into the system, the gas pressure detected by the pressure detector will rise. For example, in a prototype of the present embodiment, the pressure in the by-pass passageways rises by about 100 millibars ($10^4$ Pa) when a correctly functioning probe is connected. If the probe is connected but has a blockage, the detected pressure will rise further.

Accordingly, the output of the pressure detector can be compared with a first threshold (e.g. $10^4$ Pa over atmospheric pressure, or alternatively $1.1 \times 10^5$ Pa), with cooling operation being inhibited if the detected pressure is below that threshold. A warning light (not shown) could be illuminated on the control console to indicate that the probe is not connected. (This could be particularly useful in a multichannel system where a probe could be connected to one of several fluid outlets: the system would prevent fluid being sent to an outlet when the probe was accidentally connected to another outlet).

Similarly, if the detected pressure exceeds another threshold (e.g. $2 \times 10^4$ Pa over atmospheric pressure or alternatively $1.2 \times 10^4$ Pa) then operation could again be inhibited, with a further warning light (not shown) indicating a probe fault being illuminated.

What is claimed is:

1. A cryosurgical instrument tip for a cryosurgical instrument cooled by vaporization of liquid cryogen within the tip, the tip comprising:

a tip casing;

a boiling region within the tip casing for vaporization of the liquid cryogen; and a metal heat exchange conduit device located within the tip casing, the heat exchange conduit device defining at least partly one or more first passages for channeling cryogenic fluid between the heat exchange conduit device and the tip casing, the heat exchange conduit device being in thermal contact with the tip casing substantially entirely along the length of the heat exchange conduit device to provide thermal coupling between the tip casing and the cryogenic fluid flowing in said one or more first passages;

wherein the metal heat exchange conduit device further comprises a second conduit passage within the heat exchange conduit device for allowing cryogenic fluid to flow within the heat exchange conduit device.

2. A cryosurgical instrument tip according to claim 1, wherein the second passage is an inlet passage for allowing the flow of cryogenic fluid to the tip, and the one or more first passages are outlet passages for allowing the flow of cryogenic fluid from the tip.

3. A cryosurgical instrument tip according to claim 1, wherein the heat exchange conduit device forms a screw threaded connection with the tip casing.

4. A cryosurgical instrument tip according to claim 1, wherein the heat exchange conduit device has longitudinal flats on its outer surface to define said one or more first passages between the heat exchange conduit device and the tip casing.

5. A cryosurgical instrument tip according to claim 1, wherein an outer surface of the tip casing is coated with a heat insulating coating.

6. A cryosurgical instrument tip according to claim 5, in which substantially the entire exterior surface of the tip casing is coated with the heat-insulating coating.

7. A cryosurgical instrument tip according to claim 5, in which the coating is a polytetrafluroethane coating.

8. A cryosurgical instrument tip according to claim 5, in which the coating is less than $30 \times 10^{-6}$ meters thick.

9. A cryosurgical instrument tip according to claim 1, wherein the tip casing is made of silver.

10. A cryosurgical instrument according to claim 1, wherein the second passage is a central bore through the heat exchange conduit device.

11. A cryosurgical instrument comprising:

an instrument tip as defined in claim 1;

an instrument handle coupled to the tip; and a supply conduit for communicating cryogenic fluid from a supply to the instrument tip.

12. A cryosurgical instrument according to claim 11, wherein the instrument includes a probe, and the handle is a probe handle coupled to the instrument tip by a probe shaft.

13. A cryosurgical instrument according to claim 12, wherein the probe shaft comprises a cryogen supply conduit surrounded by an evacuated heating insulating chamber.

14. A cryosurgical instrument according to claim 11, wherein the cryogen is liquid nitrogen.

15. A cryosurgical instrument according to claim 11, further comprising a gas supply for supplying gas at greater than 0° Centigrade to the interior of the tip.

16. A cryosurgical instrument according to claim 11, wherein the second passage is an inlet passage for allowing the flow of cryogenic fluid to the tip, and the one or more first passages are outlet passages for allowing the flow of cryogenic fluid from the tip.

17. A cryosurgical instrument according to claim 11, wherein the heat exchange conduit device forms a screw threaded connection with the tip casing.

18. A cryosurgical instrument according to claim 11, wherein the heat exchange conduit device has longitudinal flats on its outer surface to define said passages between the heat exchange conduit device and the tip casing.

19. A cryosurgical instrument according to claim 11, wherein an outer surface of the tip casing is coated with a heat insulating coating.

20. A cryosurgical instrument according to claim 19, in which substantially the entire exterior surface of the tip casing is coated with the heat-insulating coating.

21. A cryosurgical instrument according to claim 19, in which the coating is a polytetrafluroethane coating.

22. A cryosurgical instrument according to claim 19, in which the coating is less than $30 \times 10^{-6}$ meters thick.

23. A cryosurgical instrument according to claim 11, wherein the tip casing is made of silver.

24. A cryosurgical instrument according to claim 11, wherein the second passage is a central bore through the heat exchange conduit device.

\* \* \* \* \*